(12) United States Patent
Mercereau et al.

(10) Patent No.: US 6,676,668 B2
(45) Date of Patent: Jan. 13, 2004

(54) ARTICULATING STONE BASKET

(75) Inventors: Steve Mercereau, Conyers, GA (US); Ken Butcher, Conyers, GA (US); Gregg A. VanDusseldorp, Crown Point, IN (US); Demetrius Bagley, Philadelphia, PA (US); Frank Bimbo, Lawrenceville, GA (US)

(73) Assignee: C.R. Baed, Murray Hill, NJ (US)

( * ) Notice: Subject to any disclaimer, the term of this patent is extended or adjusted under 35 U.S.C. 154(b) by 0 days.

(21) Appl. No.: 10/020,749

(22) Filed: Dec. 12, 2001

(65) Prior Publication Data

US 2003/0109888 A1 Jun. 12, 2003

(51) Int. Cl.⁷ ............................................. A61B 17/22
(52) U.S. Cl. .................................... 606/127; 606/1
(58) Field of Search ..................... 606/1, 106, 108, 606/110, 113, 114, 127, 128, 200, 150; 600/562

(56) References Cited

U.S. PATENT DOCUMENTS

| | | |
|---|---|---|
| 4,256,113 A | 3/1981 | Chamness |
| 4,326,530 A | 4/1982 | Fleury, Jr. |
| 4,467,802 A | 8/1984 | Maslanka |
| 4,471,777 A | 9/1984 | McCorkle, Jr. |
| 4,741,335 A | 5/1988 | Okada |
| 4,807,626 A | 2/1989 | McGirr |
| 4,997,435 A | 3/1991 | Demeter |
| 5,084,054 A | 1/1992 | Bencini et al. |
| 5,108,406 A | 4/1992 | Lee |
| 5,163,942 A | 11/1992 | Rydell |
| 5,190,557 A | 3/1993 | Borodulin |
| 5,201,741 A | 4/1993 | Dulebohn |
| 5,224,954 A | 7/1993 | Watts et al. |
| 5,312,417 A | 5/1994 | Wilk |
| 5,387,219 A * | 2/1995 | Rappe ..................... 606/108 |
| 5,387,291 A | 2/1995 | Rappe |
| 5,417,684 A | 5/1995 | Jackson et al. |
| 5,417,697 A | 5/1995 | Wilk et al. |
| 5,496,330 A | 3/1996 | Bates et al. |
| 5,522,819 A | 6/1996 | Graves et al. |
| 5,556,376 A | 9/1996 | Yoon |
| 5,613,973 A | 3/1997 | Jackson et al. |
| 5,817,104 A | 10/1998 | Bilitz et al. |
| 5,989,266 A | 11/1999 | Foster |
| 6,053,934 A | 4/2000 | Andrews et al. |
| 6,090,129 A | 7/2000 | Ouchi |
| 6,096,053 A | 8/2000 | Bates |
| 6,099,534 A * | 8/2000 | Bates et al. ................ 606/127 |
| 6,159,220 A | 12/2000 | Gobron et al. |
| 6,168,603 B1 | 1/2001 | Leslie et al. |
| 6,174,318 B1 * | 1/2001 | Bates et al. ................ 606/127 |
| 6,280,451 B1 | 8/2001 | Bates et al. |
| 6,419,639 B2 * | 7/2002 | Walther et al. ............ 600/562 |
| 6,458,145 B1 * | 10/2002 | Ravenscroft et al. ...... 606/200 |
| 2002/0019594 A1 | 2/2002 | McClellan et al. |
| 2002/0068943 A1 | 6/2002 | Chu et al. |
| 2002/0068944 A1 | 6/2002 | White et al. |

\* cited by examiner

*Primary Examiner*—Kevin Shaver
*Assistant Examiner*—Michael B. Priddy
(74) *Attorney, Agent, or Firm*—Kilpatrick Stockton LLP

(57) ABSTRACT

A medical retrieval device includes a handle, two gear racks movably mounted to the handle for longitudinal movement, and a pinion rotatably mounted to the handle so as to engage the two gear racks. Rotation of the pinion moves the gear racks in opposite directions. A basket has at least three legs, an adjacent two of the legs being connected to one of the gear racks, and the remainder of the legs being connected to the other gear rack such that rotation of the pinion displaces the two legs in a first direction and displaces the remainder of the legs in a second direction. Thus rotation of the pinion articulates the basket.

16 Claims, 13 Drawing Sheets

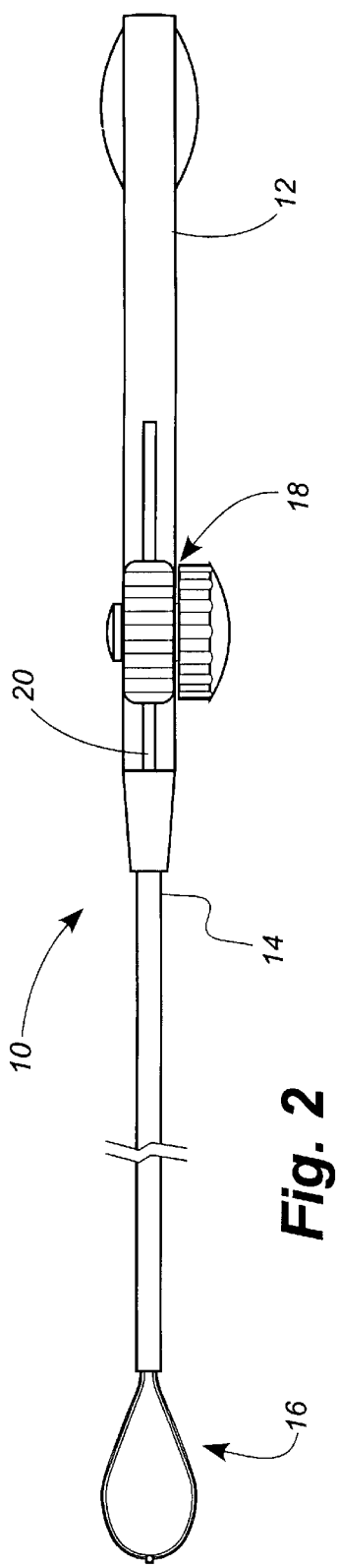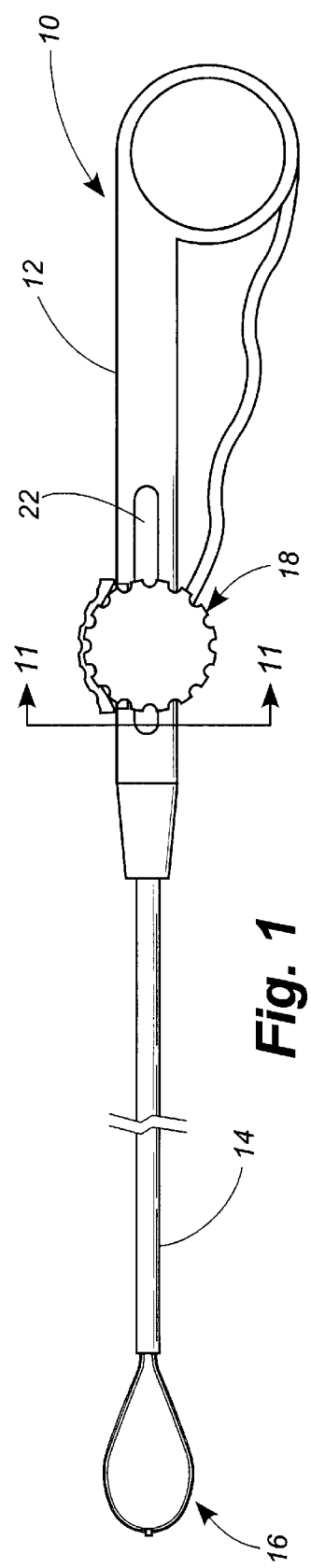

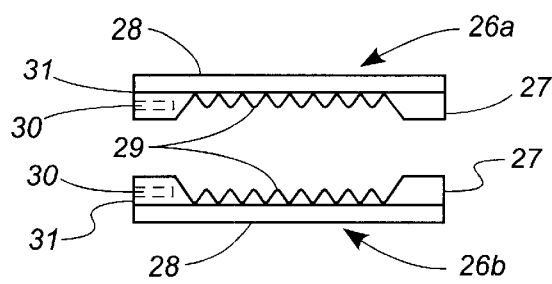
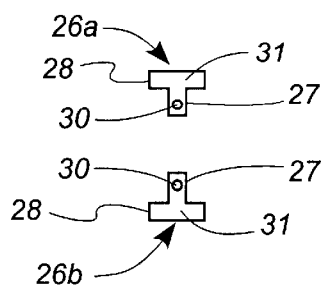
Fig. 3
Fig. 4
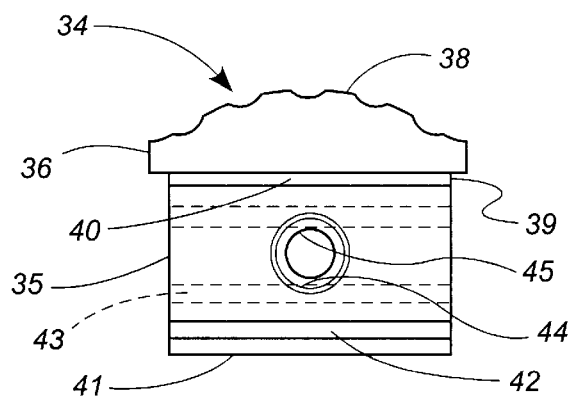
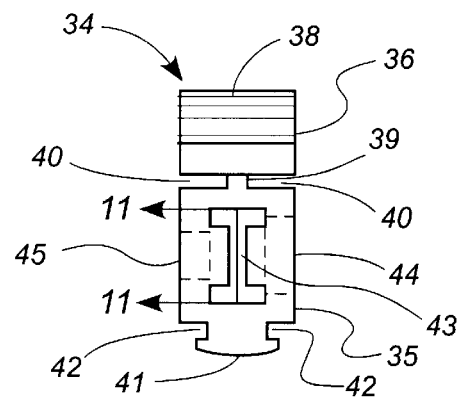
Fig. 5
Fig. 6
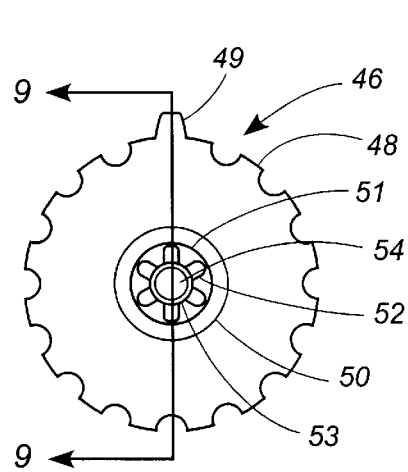
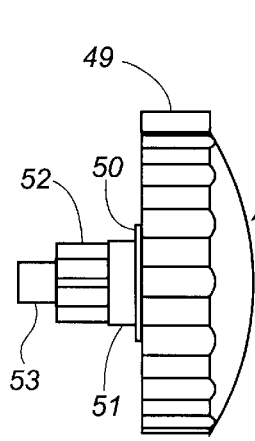
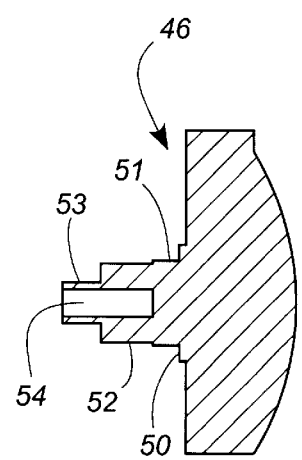
Fig. 7
Fig. 8
Fig. 9

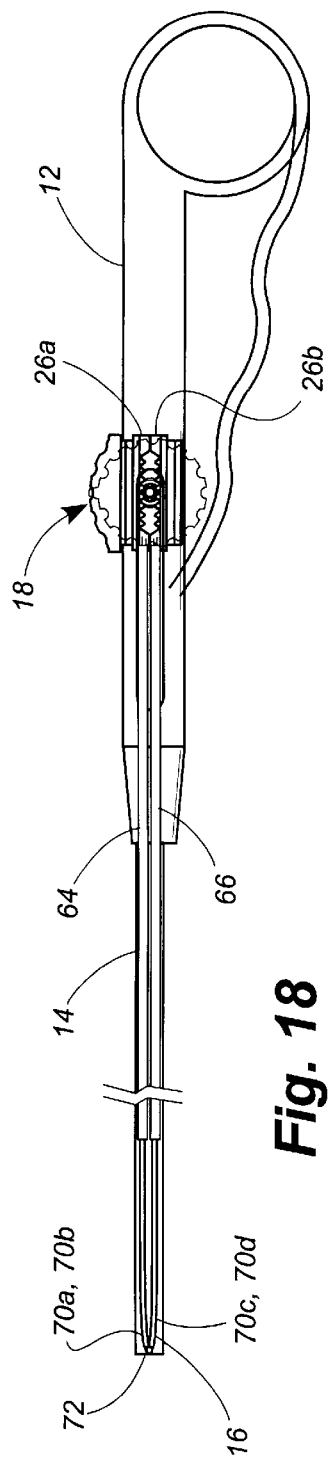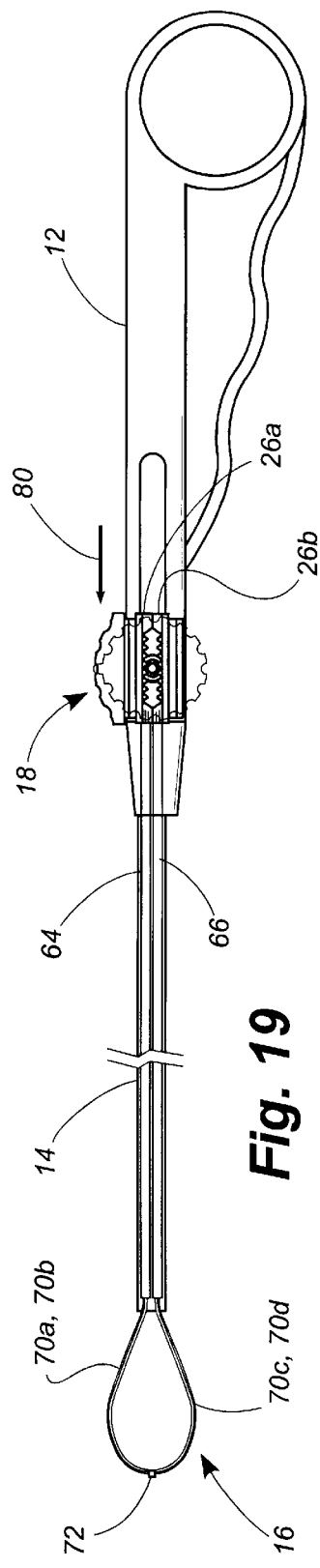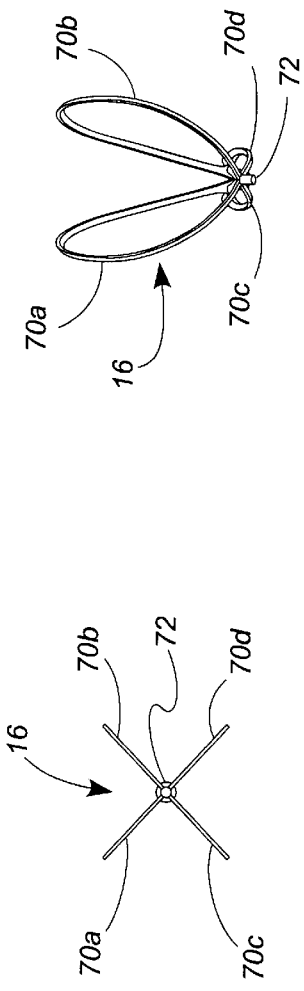

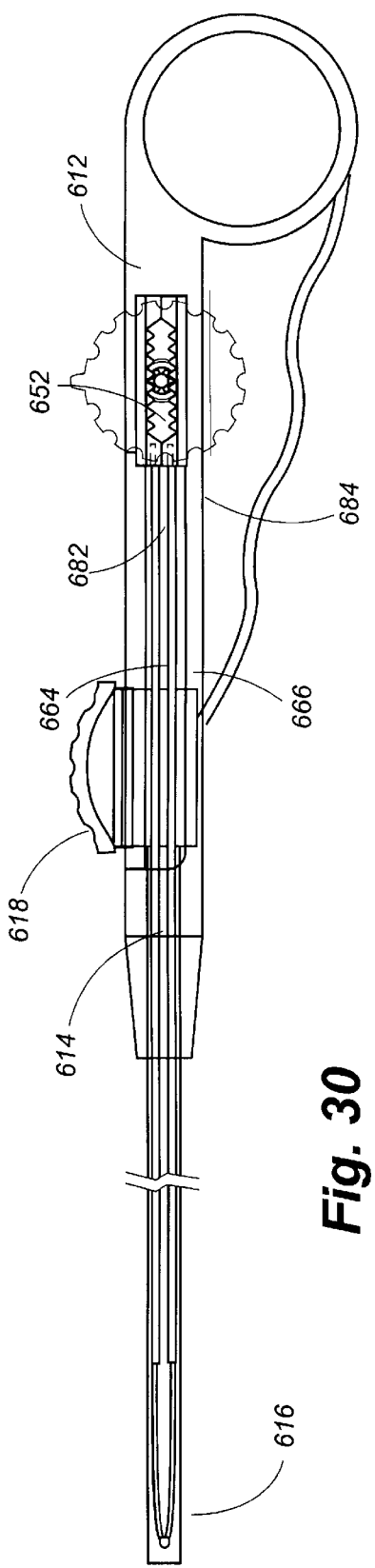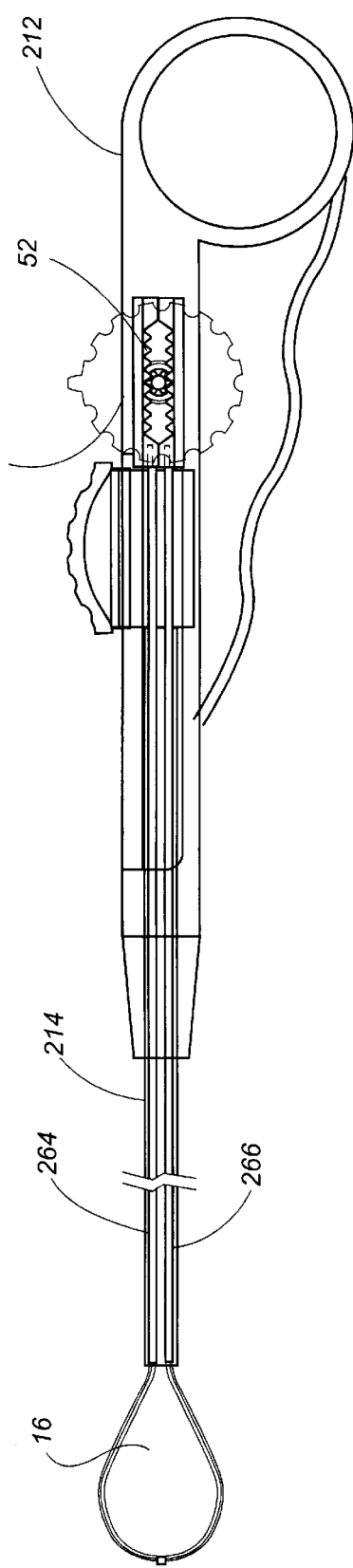
Fig. 30
Fig. 31

ARTICULATING STONE BASKET

TECHNICAL FIELD

The present invention relates generally to surgical retrieval instruments and relates more specifically to a stone basket or medical retrieval device in which the basket can be articulated.

BACKGROUND OF THE INVENTION

Medical retrieval devices or stone baskets for capturing and extracting stones from ureters are well known. Such instruments typically comprise a basket at the forward end of an elongated sheath. Wires disposed within the sheath connect the basket to a handle at the opposite end of the sheath. Various mechanisms for expanding and contracting the basket may be associated with the handle.

Today's stone baskets are being used for purposes other than simply capturing a stone in a ureter. They must also be able to reach the kidney, capture a stone, reposition it, remove it, or hold it for adjunctive treatment. Larger baskets can capture larger stones but perform poorly in capturing smaller stones. Known medical retrieval devices cannot readily release a stone if complications arise and there is a need to exit quickly. On occasion, a physician may actually have to cut the basket wires in order to release a stone, which presents the obvious complication of having to extract the basket wires from the patient.

Many conventional medical retrieval devices have tips at their forward ends for joining the legs of the basket. Such "tipped" medical retrieval devices usually have to be maneuvered alongside the stone to permit the stone to enter the basket laterally. Tipped medical retrieval devices thus present special challenges when a stone is located directly ahead of the basket and lodged against an obstruction, such as the wall of a kidney, which prevents the basket from being maneuvered alongside the stone.

SUMMARY OF THE INVENTION

Stated generally, the present invention comprises a medical retrieval device. The device includes a handle, two gear racks movably mounted to the handle for longitudinal movement, and a pinion rotatably mounted to the handle so as to engage the two gear racks. Rotation of the pinion moves the gear racks in opposite directions. A basket has at least three legs, an adjacent two of the legs being connected to one of the gear racks, and the remainder of the legs being connected to the other gear rack such that rotation of the pinion displaces the two legs in a first direction and displaces the remainder of the legs in a second direction. Thus rotation of the pinion articulates the basket.

In one embodiment of the invention a sheath extends from the front of the handle, and the basket is located at the forward end of the sheath. A slide is mounted to the handle for longitudinal movement, and the gear racks and pinion are mounted to the slide. Movement of the slide extends or retracts the basket with respect to the sheath.

In another embodiment of the invention the sheath is coupled to the slide and extends or retracts as the slide is translated. The gear racks and pinion are mounted to the handle at a longitudinally fixed position. Rotation of the pinion articulates the basket, while translation of the slide moves the sheath to cover or expose the basket.

In the disclosed embodiments the slide assembly is moved along its longitudinal path by the operator applying pressure with his thumb to a button on the top of the slide assembly. Also in the disclosed embodiments, a thumb wheel is operatively associated with the pinion such that rotation of the wheel by the operator's thumb causes the pinion to rotate to articulate the basket.

In another aspect the invention relates to a basket for a medical retrieval device and to a method for manufacturing the basket. The basket has the forward ends of its legs mounted to a tip member. In one embodiment the tip member has a hole, the forward ends of the tip members are inserted into the hole, and the tip member is crimped to clamp the legs to the tip member.

A special feature of the disclosed embodiments is the capability of a tipped basket to articulate to such a degree that the tip is moved to a location rearward of the forward extent of the basket. This capability permits the basket to open forwardly to permit an object directly ahead of the basket to enter the basket without having to maneuver the basket alongside the stone. Thus stones which are lodged against an obstruction such as the wall of a kidney which could normally not be retrieved with a tipped basket can be retrieved with the medical retrieval device of the disclosed embodiment.

Another special feature of the disclosed embodiment is that, after having grasped a stone, the basket is capable of releasing it. Thus if a physician begins to withdraw a stone and finds it is too large to pass through a physiological constriction such as the intramural ureter, or if complications arise which require rapid extraction of the medical retrieval device, the physician can articulate the basket to spread the basket wires, thereby releasing the stone.

Other objects, features, and advantages of the present invention will become apparent upon reading the following specification, when taken in conjunction with the drawings and the appended claims.

BRIEF DESCRIPTION OF THE DRAWINGS

FIG. 1 is a side view of a medical retrieval device according to a preferred embodiment of the invention.

FIG. 2 is a top view of the medical retrieval device of FIG. 1.

FIG. 3 is a side view of gear racks of the medical retrieval device of FIG. 1.

FIG. 4 is a front view of the gear racks of FIG. 3.

FIG. 5 is a side view of a slide of the medical retrieval device of FIG. 1.

FIG. 6 is a front view of the slide of FIG. 5.

FIG. 7 is a side view of a thumb wheel of the medical retrieval device of FIG. 1.

FIG. 8 is a front view of the thumb wheel of FIG. 9.

FIG. 9 is a cross-sectional view taken along line 9—9 of FIG. 7

FIG. 18 is a side cutaway view of the medical retrieval device of FIG. 1 with the basket in a retracted position.

FIG. 19 is a side cutaway view of the medical retrieval device of FIG. 1 with the basket in an extended position.

FIG. 20 is a front view of the basket in the extended position of FIG. 19.

FIG. 22 is a front view of the basket in the extended and articulated position of FIG. 21.

FIGS. 24–27 are perspective views showing the use of the medical retrieval device of FIG. 1 to retrieve a stone from a lumen, in which:

FIG. 24 shows the basket in its normal, extended position;

FIG. 25 shows the basket in its articulated position, open and ready to receive a stone;

FIG. 26 shows the basket in its articulated position maneuvered to position the basket around the stone; and FIG. 27 shows the basket retracted to capture the stone.

FIG. 30 is a side view of an alternate embodiment of a medical retrieval device in which the sheath is connected to the slide for movement with respect to the handle, showing the sheath in an extended position so as to cover the basket.

FIG. 31 is a side view of the alternate embodiment of FIG. 30 showing the sheath in a retracted position so as to expose the basket.

DETAILED DESCRIPTION OF THE DISCLOSED EMBODIMENT

Figure 10:
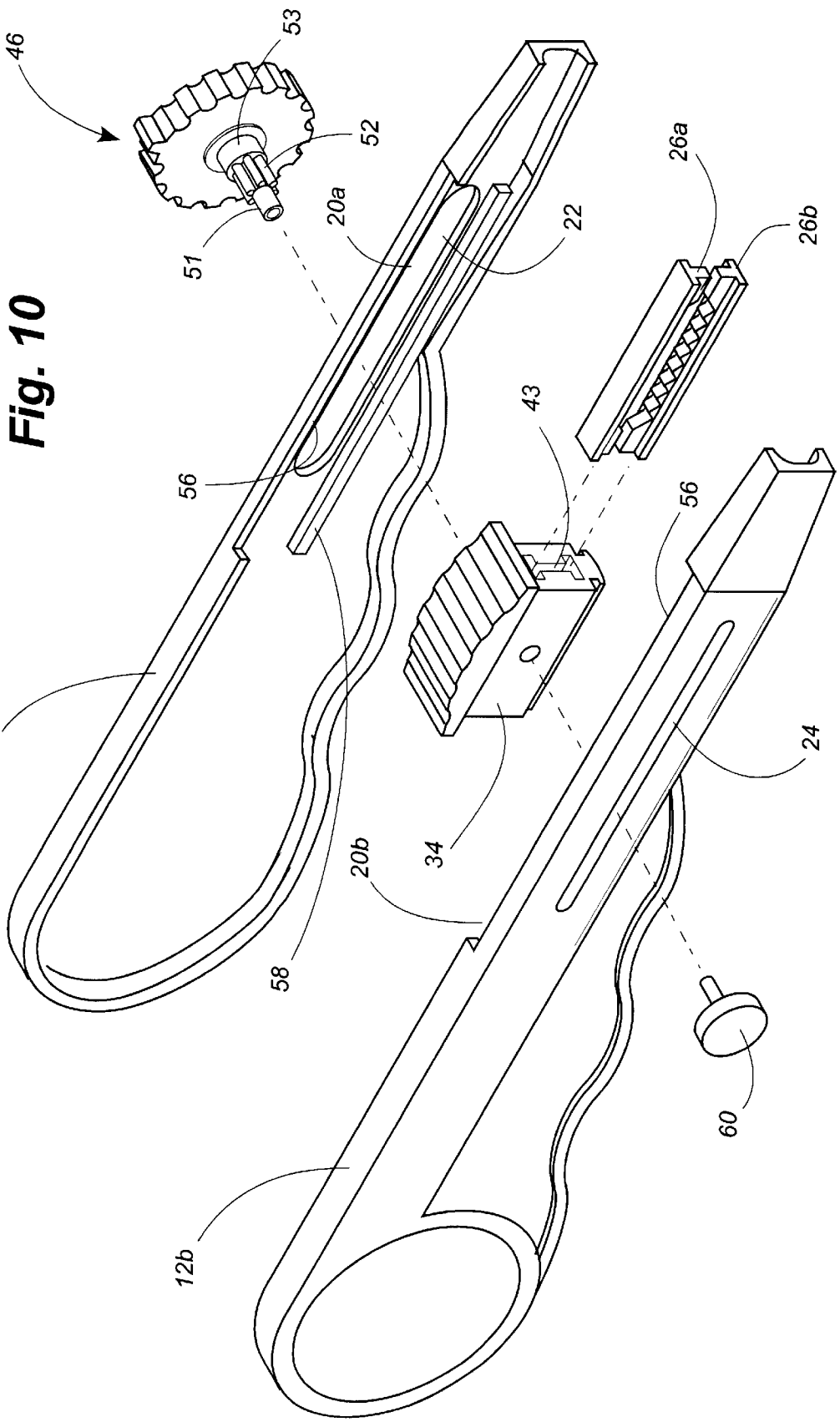
FIG. 10 is an exploded perspective view of the handle and slide assembly of the medical retrieval device of FIG. 1.

Referring now to the drawings, in which like numerals indicate like elements throughout the several views, FIGS. 1 and 2 show a medical retrieval device 10. The medical retrieval device 10 includes a handle 12, a sheath 14 attached to the forward end of the body, a basket 16 extending from the forward end of the sheath 14, and a slide assembly 18 slidably mounted to the body 12. A longitudinal slot 20 (FIG. 1) is formed in the upper edge of the handle 12. A channel 22 (FIG. 2) is formed in one lateral face of the handle, and a second channel 24 (see FIG. 12) is formed in the opposite lateral face of the handle.

FIGS. 3 and 4 show upper and lower gear racks 26a, 26b. The gear racks are identical, with the exception that the upper gear rack 26a is inverted with respect to the lower gear rack 26b. Each of the gear racks 26a, 26b includes a vertical member 27 and a transverse base 28 mounted to one edge of the vertical member. A plurality of gear teeth 29 are formed in the edge of the vertical member 27 opposite the base 28.

A passage 30 is formed in the front face 31 of each of the gear racks 26a, 26b.

FIGS. 5 and 6 show a thumb slide 34 of the slide assembly 18. The thumb slide 34 includes a body portion 35 and a button member 36 atop the body portion 35 and adapted to receive the thumb of the operator. The button member 36 includes a ribbed upper surface 38 to minimize slippage of the operator's thumb on the button member 36. A narrowed neck portion 39 joins the button member 36 to the body portion 35. Longitudinally extending recesses 40 are formed between the body portion 35 and the button member 36 along either side of the neck portion 39. At the lower edge of the body portion 35 is a foot member 41 having a rounded lower surface. A race 42 is formed in each lateral edge of the foot member 41.

An "I"-shaped channel 43 extends longitudinally through the body portion 35 of the thumb slide 34. The "I"-shaped channel 43 includes horizontal upper and lower channel sections configured to receive the bases 28 of the gear racks 26a, 26b. The upper and lower horizontal channel sections are joined by a vertical channel section which is configured to receive the vertical members 27 of the gear racks 26a, 26b.

A first transverse bore 44 is formed in one lateral face of the body portion 35 of the thumb slide 34 and extends into the I-shaped channel 43. A second transverse bore 45 coaxial with the first bore 44 and having a smaller diameter than the first bore is formed in the opposite lateral face of the body portion 35 and extends into the I-shaped channel 43.

FIGS. 7–9 depict a thumb wheel 46 of the slide assembly 18. The thumb wheel 46 has a ribbed periphery 48 adapted to receive the operator's thumb. A tab 49 is formed at the twelve o'clock position on the thumb wheel 46 to provide a visual and tactile indicator of the angular orientation of the wheel.

The thumb wheel 46 has a concentric, disk-shaped boss 50 formed on its inner surface. A cylindrical axle 51 is formed concentric with the boss 50 and extends inward from the thumb wheel 46. The axle 51 is dimensioned to fit within the first transverse bore 44 of the thumb slide 34. A pinion 52 is formed coaxial with the axle 51 and includes a plurality of teeth adapted to engage the gear teeth on the upper and lower gear racks 26a, 26b. A cylindrical extension 53 is formed on the side of the pinion 52 opposite the axle 51 and coaxial therewith. The cylindrical extension 53 is configured to be received within the second transverse bore 45 in the thumb slide 34. A threaded bore 54 is formed in the free end of the extension 53.

FIG. 10 is an exploded view of the handle 12 and slide assembly 18. The handle 12 includes mating handle halves 12a, 12b which are essentially mirror images of one another. One of the handle halves 12a, 12b includes locator pins (not shown), and the other handle half includes corresponding locator holes (also not shown) which receive the pins in the opposite handle half to align the handle halves. The two handle halves 12a, 12b are then adhesively bonded together.

Each of the handle halves 12a, 12b includes a longitudinal recess 20a, 20b in its upper surface. The outer boundary of each of the longitudinal recesses 20a, 20b is defined by a slot wall 56. When the handle halves are assembled, the longitudinal recesses 20a, 20b together form the longitudinal slot 20 (FIG. 1).

The channel 22 formed in the first handle half 12a is dimensioned to receive the axle 51 of the thumb wheel 34 therethrough. The channel 24 in the second handle half 12b is horizontally and longitudinally aligned with the channel 22 in the opposite handle half 12a and is dimensioned to receive the cylindrical extension 53 of the thumb wheel 34 therethrough.

Immediately beneath the channels 22, 24, a longitudinally extending rib 58 is formed on the inner wall of each handle half 12a, 12b. When the handle halves 12a, 12b are assembled, the ribs 58 extend toward one another, but their ends are spaced apart.

Figure 11:
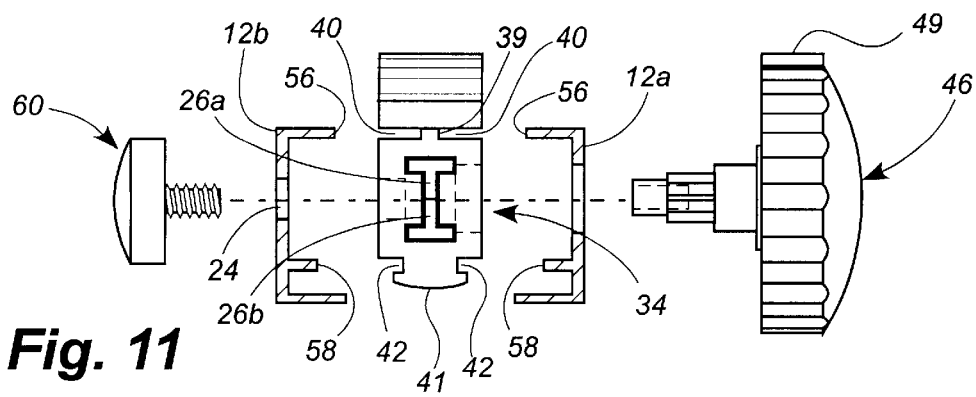
FIG. 11 is an exploded cross-sectional view of the handle and slide assembly taken along line 11—11 of FIG. 1.
Figure 12:
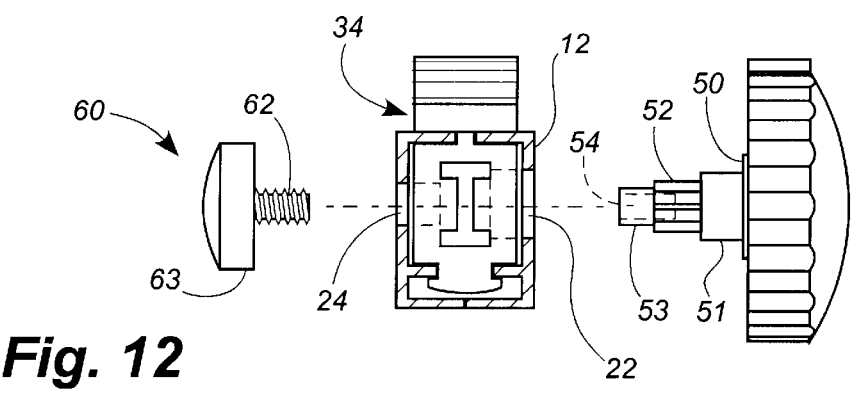
FIG. 12 is a partially exploded cross-sectional view of the handle and slide assembly taken along line 11—11 of FIG. 1, with the handle and thumb slide assembled and the thumb wheel exploded.

Assembly of the handle 12 and slide assembly 18 will now be explained with respect to FIGS. 10–13. Referring first to FIG. 10, the upper and lower gear racks 26a, 26b are inserted into either end of the I-shaped channel 43 in the thumb slide 34 and longitudinally centered with respect to the thumb slide. The handle halves 12a, 12b are then assembled around the thumb slide 34. As can be seen in FIGS. 11 and 12, the walls 56 defining the outer edges of the longitudinal slot 20 fit within the recesses 40 of the thumb slide 34, and the neck 39 of the thumb slide rides within the slot 20. Similarly, the ribs 58 on the inner wall of each handle half 12a, 12b extend into the races 42 on either side of the foot 41 of the thumb slide 34. The walls 56 and ribs 58 guide the thumb slide 34 for sliding movement along a predetermined path within the handle 12.

Figure 13:
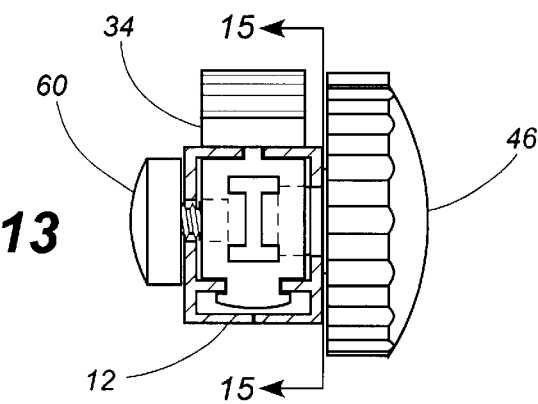
FIG. 13 is a cross-sectional view of the handle and slide assembly taken along line 11—11 of FIG. 1.

With the handle halves 12a, 12b assembled around the thumb slide 34, the cylindrical extension 53 of the thumb wheel 46 is inserted through the channel 22 in the handle half 12a and advanced to the position shown in FIG. 13. The extension 53 is located within the bore 45 of the thumb slide, the pinion 52 is engaged with the upper and lower gear racks 26a, 26b, and the axle 51 of the thumb slide is disposed within the transverse bore 44 of the thumb slide. With the pinion 52 thus engaged with the gear racks 26a, 26b, the outer end of the cylindrical extension 53 of the thumb wheel 46 rides within the channel 24 of the handle 12, the inner portion of the axle 51 rides within the channel 22 of the handle, and the boss 50 of the thumb wheel bears against the wall surrounding the channel 22 of the handle to space the thumb wheel from the surface of the handle.

Referring further to FIG. 13, to retain the thumb wheel 46 in position, a screw 60 having a threaded shank 62 and an enlarged head portion 63 is inserted into the threaded bore 54 in the end of the cylindrical extension 53 of the thumb wheel 46. The enlarged head portion 63 of the screw is larger than the slot 24 in the handle 12 and thus prevents the thumb wheel 46 from becoming laterally disengaged from the thumb slide 34 and handle.

Figure 14:
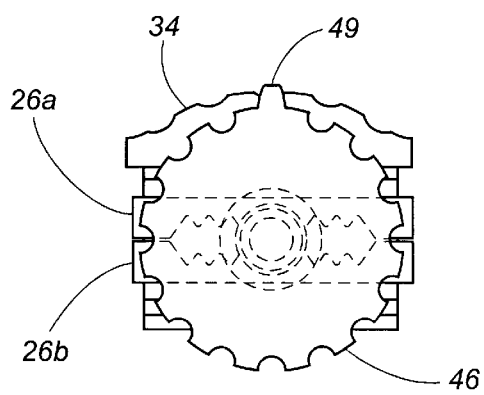
FIG. 14 is a side view of the assembled handle, slide, and thumb wheel of FIG. 13.
Figure 15:
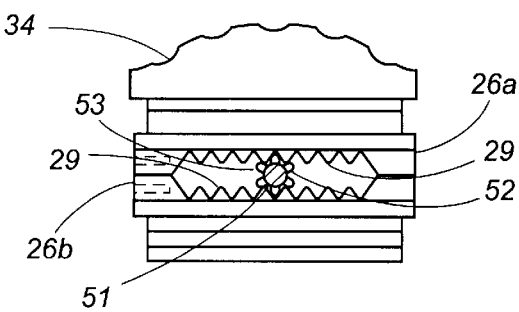
FIG. 15 is a sectional view taken along line 15—15 of FIG. 13.

Referring now to FIGS. 14 and 15, when the handle 12 and slide assembly 18 are assembled as explained above, the teeth of the pinion 52 engage the teeth 29 of the gear racks 26a, 26b.

Figure 16:
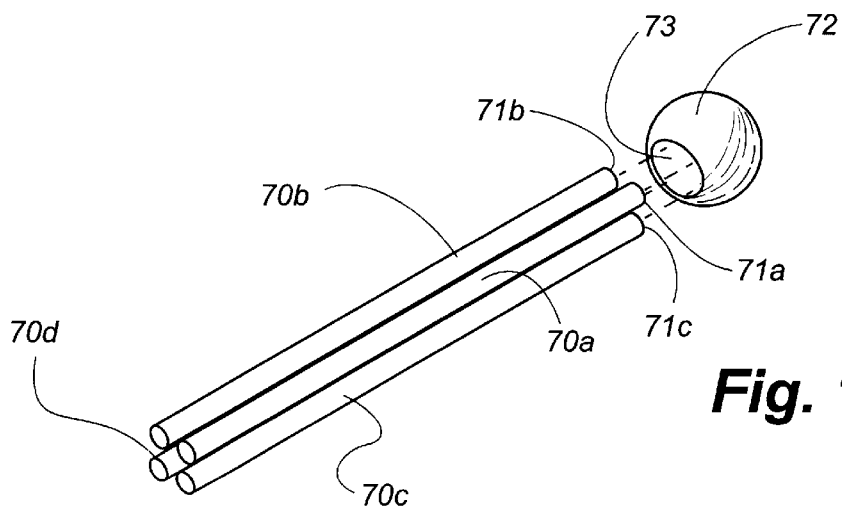
FIG. 16 is an exploded isometric view showing the assembly of the basket wires of the device of FIG. 1 onto the tip member.
Figure 17:
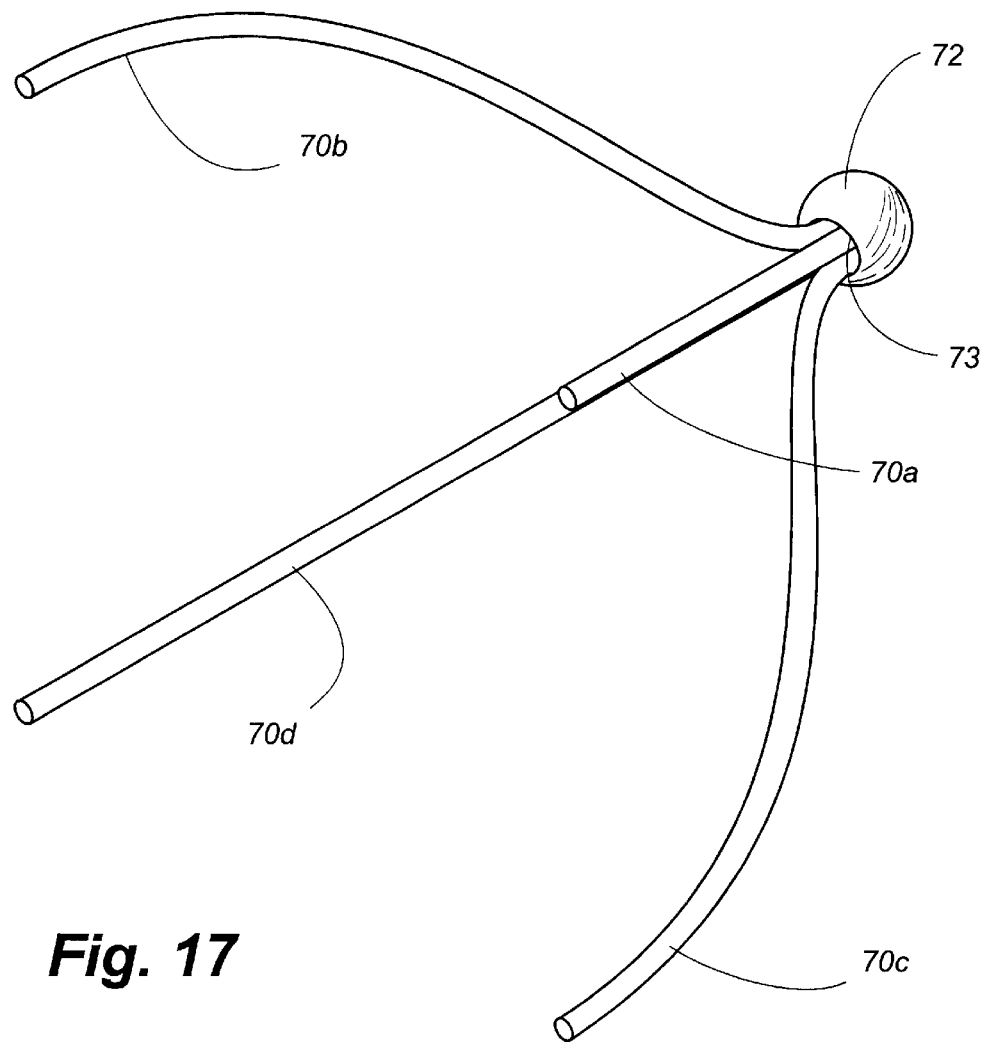
FIG. 17 is an isometric view showing the assembled basket wires and tip member of FIG. 16.

FIGS. 16 and 17 depict details of the basket 16. The basket 16 comprises four legs 70a–70d having forward ends 71a–71d respectively. A tip member 72 is made from a stainless steel ball having a hole 73 drilled therein. The forward ends 71a–71d of the wires 70a–70d are inserted into the hole 73 in the tip member 72. The tip member 72 is then crimped in a collet to capture the wires within the hole 73, in much the same way that a sinker is attached to a fishing line. The resulting structure provides a rounded tip that minimizes the chance of causing any laceration or puncture during use.

FIGS. 18–21 illustrate further details of the medical retrieval device 10. Two elongated tubes 64, 66 are telescopically disposed within the sheath 14 of the medical retrieval device 10. The basket 16 is mounted to the forward ends of the tubes 64, 66. More specifically, the rearward ends 75a, 75b of the upper two basket legs 70a, 70b are mounted to the upper tube 64, and the rearward ends 77a, 77b of the lower two basket legs 70c, 70d are mounted to the lower tube 66. (note: basket leg 70a is directly behind basket leg 70b in FIGS. 18–21, and basket leg 70c is directly behind basket leg 70d). The basket legs 70a–70d of the disclosed embodiment are secured to the tubes 64, 66 by inserting the rearward ends 75a, 75b, 77a, 77b of the legs into their respective tubes and then crimping the tube ends. However, it will be appreciated that other means for mounting the basket legs to the tubes may be employed, including adhesives, welding, and the like.

As will be appreciated from the foregoing explanation, an advantage of the tip member 72 is that the forward ends 71a–71d of the basket legs 70a–70d can be joined to the tip member after the ends rearward ends 75a, 75b, 77a, 77b of the loops have been attached to their respective tubes 64, 66, thus facilitating assembly.

The rearward ends of the tubes 64, 66 are operatively connected to the slide assembly 18 by inserting the tube ends directly into the passages 30 in the front faces 31 of the upper and lower gear racks 26a, 26b. The tubes 64, 66 are anchored to the gear racks 26a, 26b by adhering, welding, clamping, or otherwise bonding the tube ends within the passages. In the alternative, a short length of cable can be used to couple each tube to its associated gear rack. The forward end of the cable is connected to the rearward end of a tube by crimping, adhering, welding, or otherwise bonding the cable to the tube. The rearward end of the cable is inserted into the passages 30 in the front faces 31 of the upper and lower gear racks 26a, 26b and secured by adhering, welding, clamping, or otherwise bonding the tube ends within the passages. In the latter arrangement, the cable should be sufficiently stiff that an axial compressive force applied to the cable will be transferred to the opposite end of the cable without causing the cable to buckle.

Operation of the medical retrieval device 10 will now be described with respect to FIGS. 18–23. In FIG. 18, the slide assembly 18 is in a rearward position with respect to the handle 12, and the basket 16 is retracted within the forward end of the sheath 14. In FIG. 18 the tip member 72 is shown retracted within the forward end of the sheath 14. To make the sheath 14 as small a diameter as possible to facilitate introduction into the patient, while still providing a tip assembly 72 sufficiently large to make assembly of the basket 16 expedient, the tip member 72 may have a larger outer diameter than the inner diameter of the sheath 14. In this case the legs 70a–70d will be retracted within the forward end of the sheath, but the tip member 72 will abut the forward end of the sheath and remain at least partially exposed outside the sheath. For purposes of this application, the basket 70 will be considered retracted within the forward end of the sheath 14 if a major portion of the legs 70a–70d is retracted within the forward end of the sheath, even if the tip member 72 remains outside the sheath.

When the slide assembly 18 is advanced in the direction of the arrow 80, as shown in FIG. 19, the tubes 64, 66 are telescopically advanced within the sheath 14, extending the basket legs 70a–70d from the forward end of the sheath. The basket legs 70 are preferably formed from a shape memory metal such as nitinol, such that the legs, once freed from the confines of the sheath 14, spring outward into their predetermined configurations. As can be seen in FIG. 20, when the basket 16 has expanded to its predetermined configuration, the basket legs 70a–70d essentially form an "X" configuration as viewed along the longitudinal axis of the device.

Figure 21:
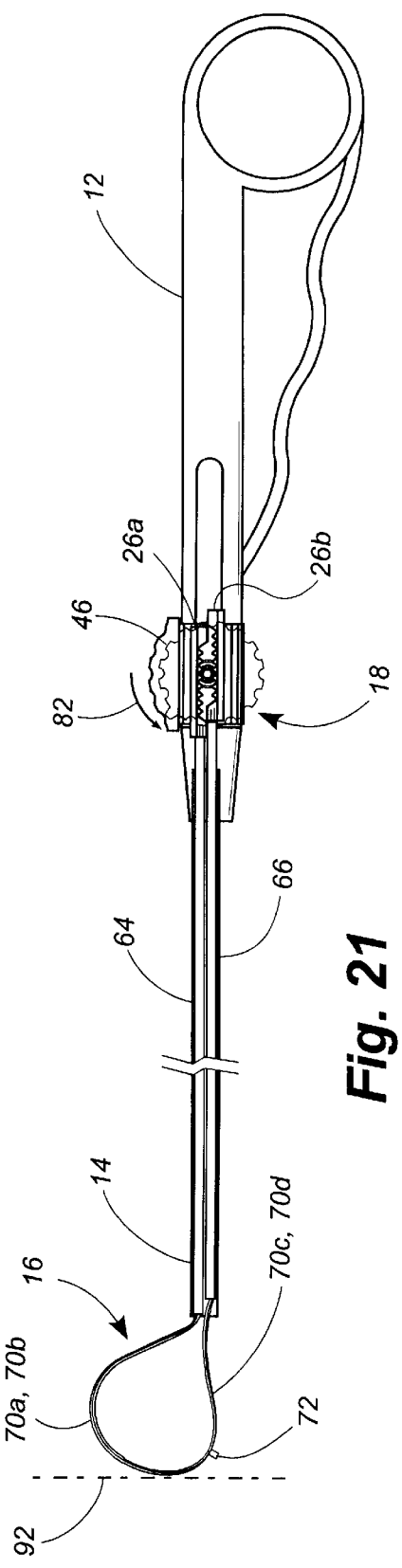
FIG. 21 is a side cutaway view of the medical retrieval device of FIG. 1 with the basket extended and articulated downward.

In FIG. 21 the thumb wheel 46 is rotated forward. This action rotates the pinion 52 in a counterclockwise direction, as shown by the arrow 82 in FIG. 21. The upper gear rack 26a is displaced forward, and the lower gear rack 26b is displaced rearward. The rearward motion of the lower gear rack 26b retracts the lower tube 66. Simultaneously the forward motion of the upper gear rack 26a advances the upper tube 64. Thus the tubes 64, 66 move in reciprocal directions. This extension of the upper tube 64 and retraction of the lower tube 66 causes the upper basket legs 70a, 70b to extend and the lower basket legs 70c, 70d to retract, thus articulating the basket 16 downward.

Referring to FIGS. 21 and 22, articulation of the basket 16 causes several advantageous effects. First, as can be seen in FIG. 21, the tip member 72 is displaced rearward of a plane 92 defined by the forward edge of the basket. Thus if a stone is lodged against a wall perpendicular to the longitudinal axis of the device 10, the tip member 72 does not prevent the basket 16 from being advanced right up against the wall to capture the stone. Second, as can be seen in FIG. 22, articulation of the basket 16 causes the two upper legs 70a, 70b to spread apart, thus making it easier to maneuver the basket around a stone.

Figure 23:
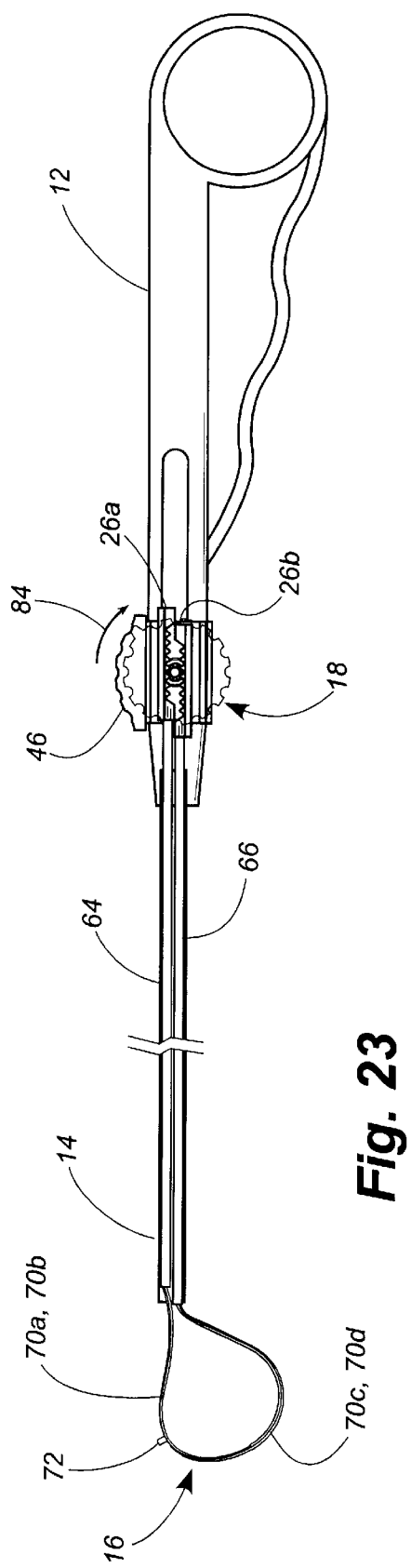
FIG. 23 is a side cutaway view of the medical retrieval device of FIG. 1 with the basket extended and articulated upward.

In FIG. 23, the thumb wheel 46 is rotated rearward. The turning of the thumb wheel rotates the pinion 52 in a clockwise direction, as indicated by the arrow 84 in FIG. 23. This rotation of the pinion 52 drives the upper gear rack 26a rearward and simultaneously drives the lower gear rack 26b forward. This reciprocal motion of the gear racks 26a, 26b retracts the upper tube 64 and advances the lower tube 66. Thus the lower basket legs 70c, 70d are extended, and the upper basket legs 70a, 70b are retracted. This causes the basket 16 to articulate upward.

Figure 24:
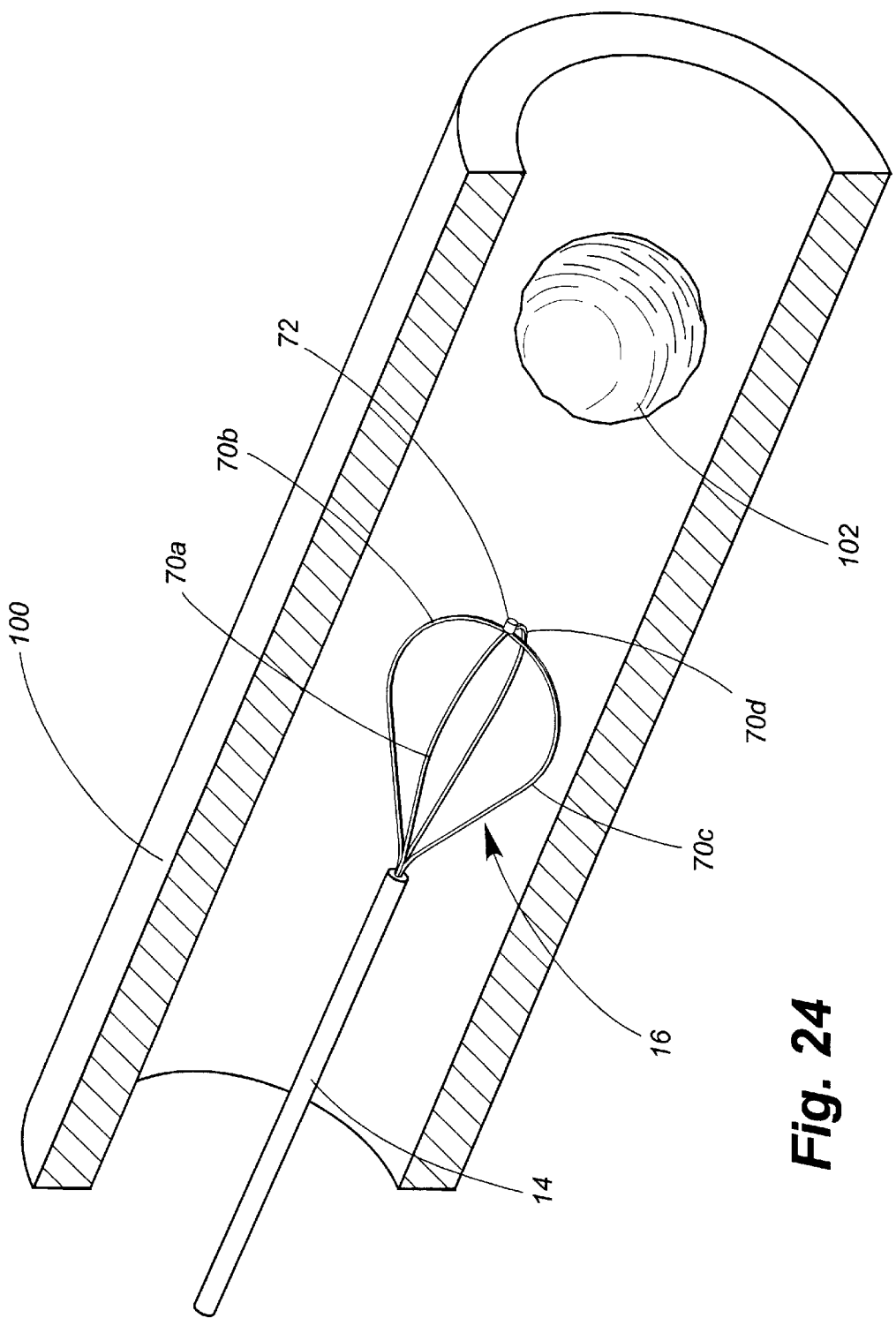

Use of the device 10 to capture a stone from the body of a patient will now be explained with reference to FIGS. 24–27. With the basket 16 retracted within the sheath 14, the forward end of the device is inserted into the patient to a location adjacent the target site. For purposes of example, the target location is a point within a duct 100 such as a ureter. As the forward end of the device nears a stone 102, the basket 16 is opened. As shown in FIG. 24, the four basket wires 70a–70d expand. In this expanded but unarticulated configuration, the tip assembly 72 is the forwardmost element of the device.

Figure 25:
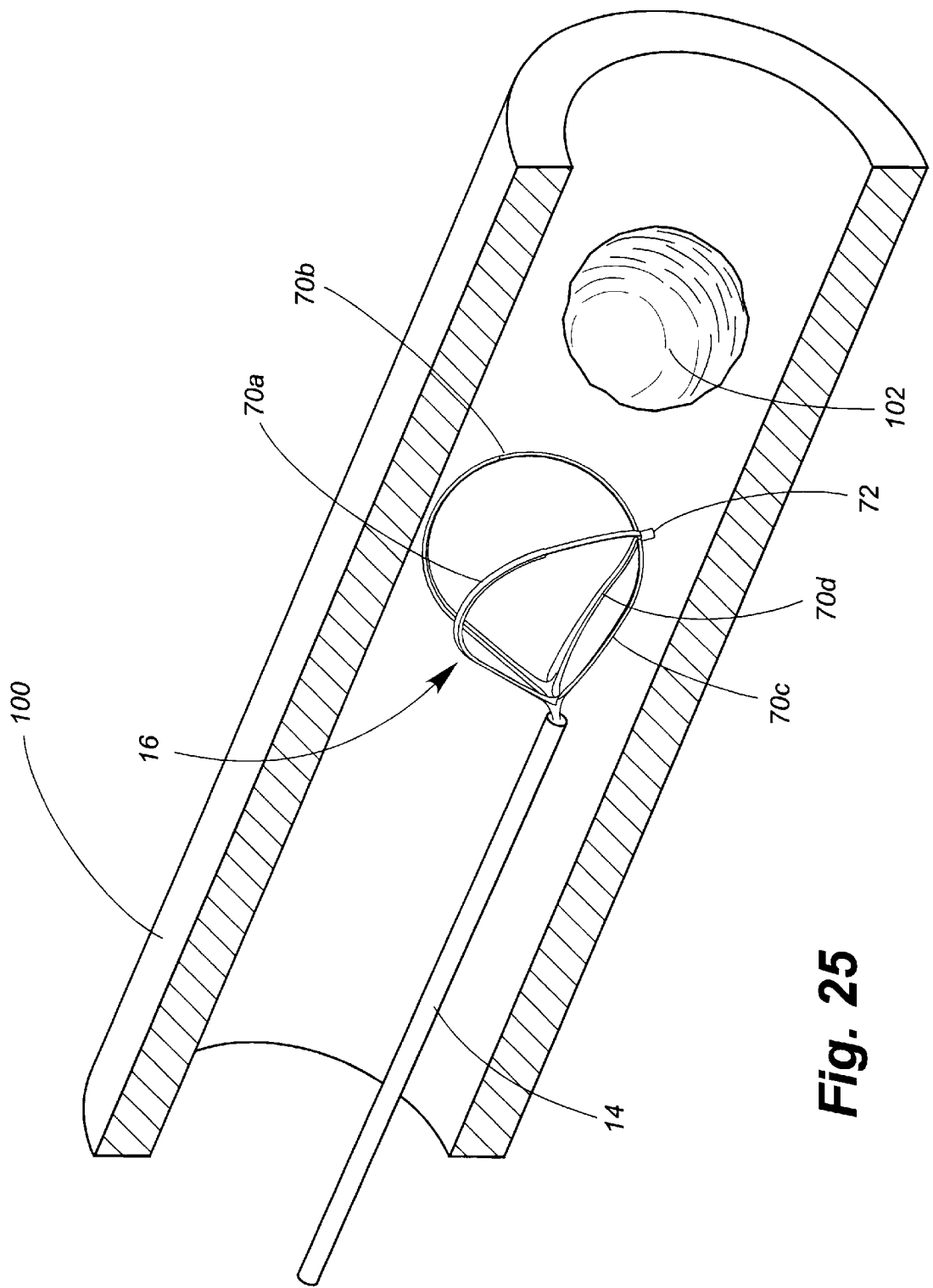

The device is then actuated to articulate the basket 16, as shown in FIG. 25. The upper two legs 70a, 70b extend, and the lower two legs 70c, 70d retract. This articulation causes the tip assembly 72 to be displaced downward and rearward, such that the tip assembly is no longer the forwardmost point of the device. In addition, articulation causes the upper two legs 70a, 70b to spread apart, thereby creating a larger opening to facilitate maneuvering the basket 16 around the stone 102.

Figure 26:
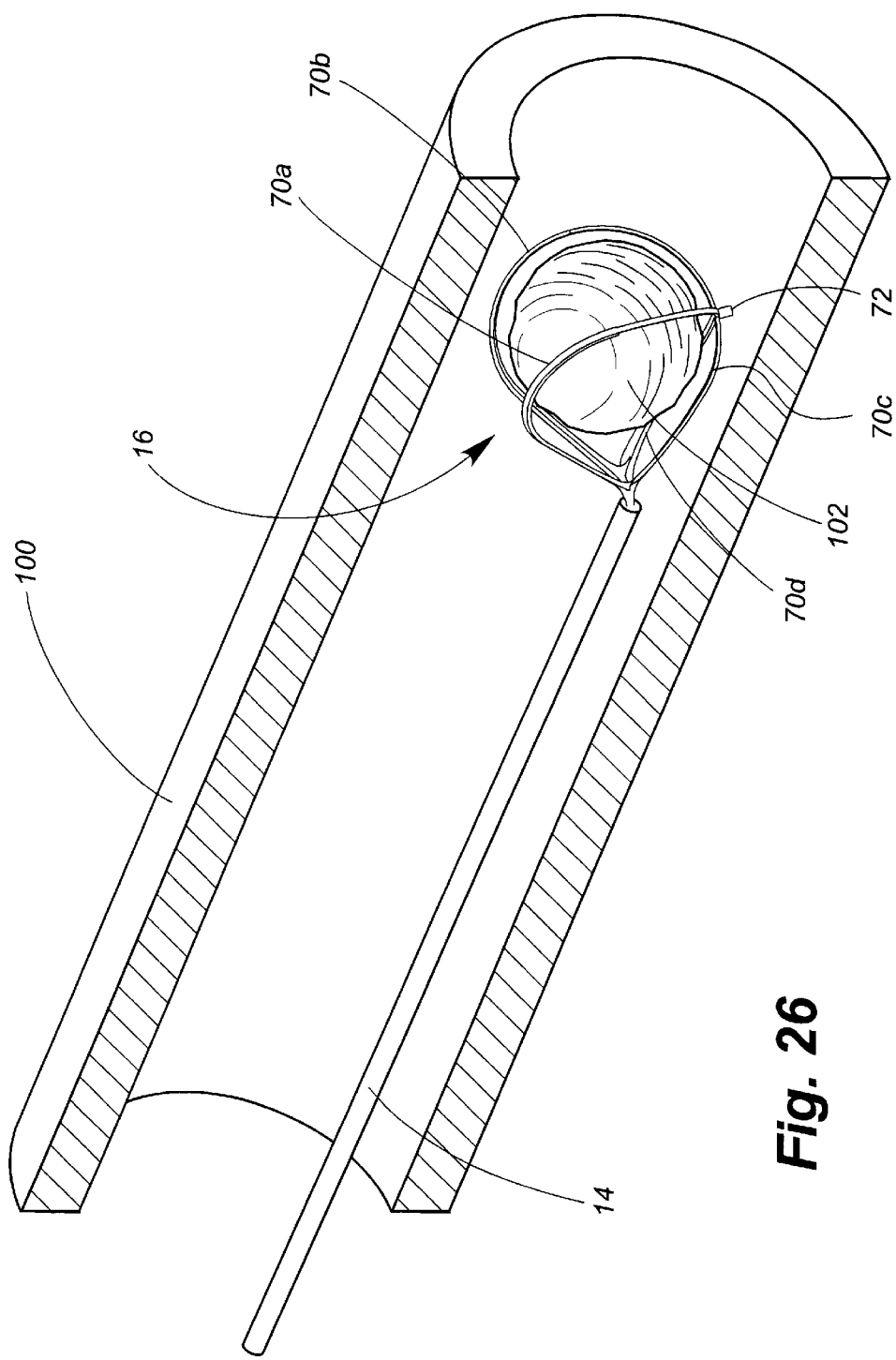
Figure 27:
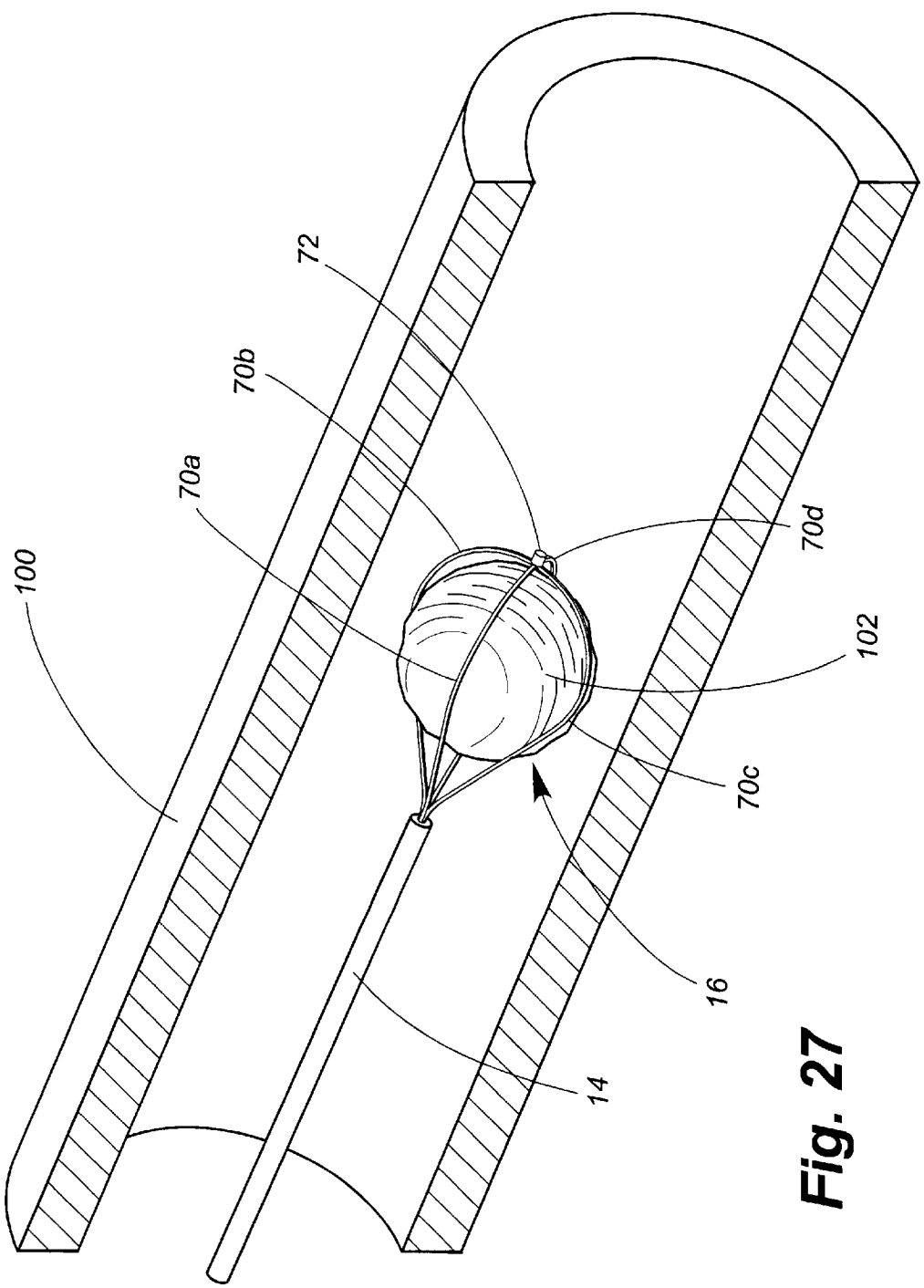

The device is now maneuvered to the position shown in FIG. 26, where the basket 16 surrounds the stone 102. The basket is then articulated back to its original position, and the device actuated to partially retract the basket 16, causing the basket legs 70a–70d to tighten around the stone 102, as shown in FIG. 27. With the stone 102 thus snared, the device is withdrawn to remove the stone from the duct 100.

If the physician begins to withdraw the stone 102 and finds it is too large to pass through a physiological constriction such as the intramural ureter, or if complications arise which require rapid extraction of the device 10, the physician can rotate the wheel 46 to articulate the basket 16 to spread the basket wires 70a–d. Thus the stone can be quickly released.

If the location of the stone 102 makes it necessary to articulate the basket 16 left and right, rather than up and down, the physician simply rotates the handle 12 by 90°. The sheath 14 has sufficient torsional stiffness to rotate along with the handle 12, such that rotation of the thumb wheel 46 will effect left or right steering of the basket 16.

The arrangement by which movement of one of the tubes 64, 66 causes an equal-but-opposite movement of the other tube provides the advantage that rotation of the thumb wheel 46 by a given amount results in twice the effective "throw." Thus less movement of the thumb wheel 46 is required to effect the same range of articulation than when only one tube is moved and the remaining tubes held stationary.

Figure 28:
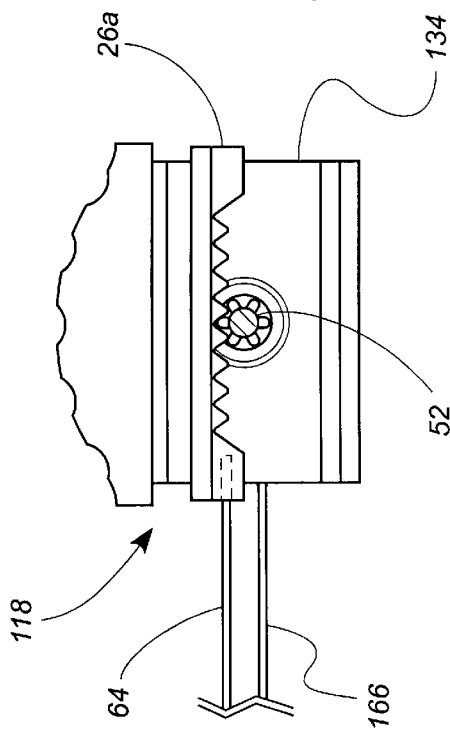
FIG. 28 is a slide assembly of an alternate embodiment of a medical retrieval device.
Figure 29:
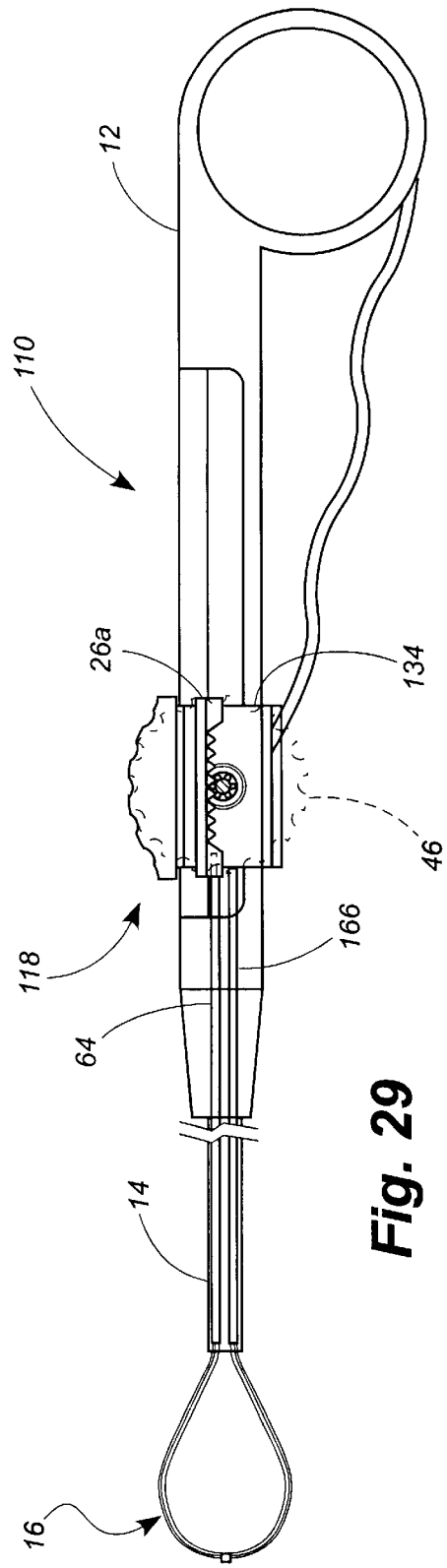
FIG. 29 is a side cutaway view of an alternate embodiment of a medical retrieval device including the slide assembly of FIG. 28.

As will be appreciated, in the embodiment 10 described above, the motion of the basket legs is dependent, that is, movement of one basket leg is necessarily accompanied by movement of all of the other legs, either in the same direction or in an opposite direction. Stated differently, in the embodiment 10 it is not possible to move any leg of the basket independently of the other legs. FIGS. 28 and 29 illustrate an alternate embodiment 110 which permits independent movement of one or more legs relative to the other legs. In the embodiment 110 the slide assembly 118 comprises only a single gear rack 26a engaging the pinion 52, and in which only one of the tubes is translated to articulate the basket 16. The upper tube 64 is mounted to the gear rack 26a in the same manner as previously described. However, the lower tube 166 is fixedly mounted to the thumb slide 134. Rotation of the thumb wheel 46 in a forward direction advances the upper tube 64 while the lower tube 166 is held steady, articulating the basket 16 downward. Rotation of the thumb wheel 46 in a rearward direction retracts the upper tube 64 while the lower tube 166 is held steady, articulating the basket 16 upward.

FIGS. 30 and 31 depict a second alternate embodiment in which, rather than the basket 16 being extended and retracted with respect to a fixed sheath, the basket 16 is fixed with respect to the handle while the sheath is extensible and retractable.

While the foregoing embodiment employs a pair of tubes 64, 66 telescopically disposed within the sheath 14 to facilitate coupling the basket legs 70a–70d to the gear racks 26a, 26b of the slide assembly 18, it will be appreciated that more than two tubes can be used to couple the basket legs 70a–70d to the gear racks 26a, 26b of the slide assembly 18. For example, each leg 70a–70d can be attached to its own tube, with more than one tube attached to a given gear rack.

Further, while the foregoing embodiment 10 provides a thumb wheel 46 which the operator turns to rotate the pinion 52 to articulate the basket 16, it will be appreciated that the thumb wheel is not essential to the operation of the device. For example, a lever coupled to the pinion 52 could be used in lieu of the thumb wheel, or an electric motor could be arranged to rotate the pinion when actuated. Similarly, while the slide assembly 18 of the embodiment 10 is manually advanced and retracted along its path of movement on the handle 12 by the operator's finger, it will be appreciated that alternate arrangements for longitudinally displacing the slide assembly with respect to the handle may be used, including an electric motor.

The basket 16 of the disclosed embodiment 10 comprises a tip member 72 having a hole 73 within which the forward ends 71a–71d of the basket legs 70a–70d are inserted and the tip member then crimped to clamp the basket legs to the tip member. However, it will be understood that the actuation device of the disclosed embodiment can also be used with a basket of conventional construction. In the alternative, the basket legs 70a–70d can be secured within the hole 73 of the tip member 72 by other means, such as adhesive or welding.

Finally, it will be understood that the preferred embodiment has been disclosed by way of example, and that other modifications may occur to those skilled in the art without departing from the scope and spirit of the appended claims.

What is claimed is:

1. A medical retrieval device comprising:
a handle;
two gear racks movably mounted with respect to said handle for longitudinal movement;
a pinion rotatably mounted with respect to said handle so as to engage said two gear racks such that rotation of said pinion moves said gear racks in opposite directions;
a basket having at least three legs, an adjacent two of said legs being connected to a first one of said gear racks, and the remainder of said legs being connected to a second one of said gear racks such that rotation of said pinion displaces said two legs in a first direction and displaces the remainder of said legs in a second direction different from said first direction.

2. The medical retrieval device of claim 1, further comprising a slide attached to said handle for longitudinal movement with respect thereto along a path between a rearward location and a forward location,
wherein said racks and said pinion are mounted with respect to said handle by said racks and said pinion being mounted to said slide, which is in turn mounted to said handle.

3. The medical retrieval device of claim 2, further comprising a hollow sheath extending forward from said handle, said sheath having a forward end, and said basket being located at a forward end of said sheath;
said basket being operatively associated with said slide such that said basket is retracted within a forward portion of said sheath when said slide is in said rearward location, and said basket is extended forward of said forward end of said sheath when said slide is in said forward location;
whereby longitudinal movement of said slide extends and retracts said basket.

4. The medical retrieval device of claim 3, further comprising a pair of tubes telescopically disposed within said sheath, a first one of said pair of tubes being connected to said first one of said gear racks, and a second one of said pair of tubes being connected to said second one of said gear racks, and wherein said adjacent two basket legs are connected to said first one of said gear racks by said adjacent two basket legs being connected to a forward end of said first tube, and wherein said remainder of said basket legs are connected to said second one of said gear racks by said remainder of said basket legs being connected to a forward end of said second tube.

5. The medical retrieval device of claim 1, further comprising:
a slide attached to said handle for longitudinal movement with respect thereto along a path between a rearward location and a forward location,
a hollow sheath mounted to said slide and extending forward from said handle, said sheath having a forward end, and said basket being located at a forward end of said sheath,
said sheath being operatively associated with said slide such that said sheath is retracted to expose said basket when said slide is in said rearward location, and said sheath is extended forward to cover said basket when said slide is in said forward location;
whereby longitudinal movement of said slide extends and retracts said sheath.

6. The medical retrieval device of claim 1, further comprising a wheel operatively associated with said pinion such that rotation of said wheel rotates said pinion to displace said basket legs.

7. The medical retrieval device of claim 1, wherein said basket further comprises a tip member, wherein said basket legs each comprise a forward end, and wherein said forward ends of said basket legs are connected to said tip member.

8. The medical retrieval device of claim 7, wherein said tip member comprises a hole formed therein, and wherein said forward ends of said basket legs are connected to said tip member by inserting said forward ends of said basket legs into said hole and anchoring said forward ends of said basket legs within said hole.

9. The medical retrieval device of claim 8, wherein said tip member is deformable, and wherein said forward ends of said basket legs are secured within said hole by inserting said forward ends of said basket legs into said hole and deforming said tip member so as to clamp said forward ends of said basket legs within said hole.

10. A medical retrieval device comprising:
a handle;
a gear rack movably mounted to said handle for longitudinal movement with respect to said handle;
a pinion rotatably mounted with respect to said handle so as to engage said gear rack such that rotation of said pinion translates said gear rack;
a basket having at least three legs, at least one of said legs being connected to said gear rack, and the remainder of said legs being connected to said handle such that rotation of said pinion translates said gear rack to move said at least one of said legs relative to the remainder of said legs.

11. The medical retrieval device of claim 10, further comprising a slide attached to said handle for longitudinal movement with respect thereto along a path between a rearward location and a forward location,
wherein said rack and said pinion are mounted with respect to said handle by said rack and said pinion being mounted to said slide, which is in turn mounted to said handle; and
wherein the remainder of said legs are connected to said handle comprises the remainder of said legs being attached to said slide, which is in turn mounted to said handle.

12. The medical retrieval device of claim 11, further comprising a hollow sheath extending forward from said handle, said sheath having a forward end, and said basket being located at a forward end of said sheath;
said basket being operatively associated with said slide such that said basket is retracted within a forward portion of said sheath when said slide is in said rearward location, and said basket being extended forward of said forward end of said sheath when said slide is in said forward location;
whereby longitudinal movement of said slide extends and retracts said basket.

13. The medical retrieval device of claim 10, further comprising:
a slide attached to said handle for longitudinal movement with respect thereto along a path between a rearward location and a forward location,
a hollow sheath mounted to said slide and extending forward from said handle, said sheath having a forward end, and said basket being located at a forward end of said sheath, said sheath being operatively associated with said slide such that said sheath is retracted to expose said basket when said slide is in said rearward location, and said sheath being extended forward to cover said basket when said slide is in said forward location;

whereby longitudinal movement of said slide extends and retracts said sheath.

14. The medical retrieval device of claim 10, further comprising a wheel operatively associated with said pinion such that rotation of said wheel rotates said pinion to displace said gear rack.

15. The medical retrieval device of claim 10, wherein each of said at least three legs comprises a forward end, and wherein said basket further comprises a tip member having a hole formed therein;

said forward end of each of said at least three legs being received within said hole in said tip member and secured therewithin.

16. The basket of claim 15, wherein said forward end of each of said at least three legs is secured within said hole in said tip member by said forward end of each of said at least three legs being inserted into said hole and said tip member being crimped so as to capture said forward end of each of said at least three legs within said hole.

\* \* \* \* \*

UNITED STATES PATENT AND TRADEMARK OFFICE
CERTIFICATE OF CORRECTION

PATENT NO. : 6,676,668 B2
DATED : January 13, 2004
INVENTOR(S) : Steve Mercereau et al.

It is certified that error appears in the above-identified patent and that said Letters Patent is hereby corrected as shown below:

Title page,
Item [73], Assignee, should read as follows:
-- C.R. Bard, Inc., Murray Hill, NJ (US) --

Signed and Sealed this

Second Day of August, 2005

JON W. DUDAS
*Director of the United States Patent and Trademark Office*